United States Patent

Klopf

Patent Number: 5,830,166
Date of Patent: Nov. 3, 1998

[54] ORTHOSIS

[76] Inventor: Michael Klopf, Bachstrasse 8, D-97297 Waldbuttelbrunn, Germany

[21] Appl. No.: 750,340

[22] PCT Filed: Apr. 19, 1995

[86] PCT No.: PCT/DE95/00545

§ 371 Date: Jan. 21, 1997

§ 102(e) Date: Jan. 21, 1997

[87] PCT Pub. No.: WO95/32691

PCT Pub. Date: Dec. 7, 1995

[30] Foreign Application Priority Data

May 26, 1994 [DE] Germany .......................... 44 18 382.8

[51] Int. Cl.[6] ...................................................... A61S 5/10
[52] U.S. Cl. ................................ 602/16; 602/16; 602/26
[58] Field of Search .................................. 602/5, 21, 28, 602/26, 20, 16; 601/33, 34; 462/115

[56] References Cited

U.S. PATENT DOCUMENTS

| 1,851,241 | 3/1932 | Dresser ..................................... 602/16 |
| 4,865,024 | 9/1989 | Hersley et al. ........................... 602/16 |
| 4,958,643 | 9/1990 | Poinsiera .................................. 602/16 |
| 5,358,469 | 10/1994 | Patchel et al. ............................. 602/5 |
| 5,399,154 | 3/1995 | Kipis et al. ............................... 602/16 |

FOREIGN PATENT DOCUMENTS

| 2477409 | 9/1981 | France ..................................... 602/16 |
| 93009734 | 5/1993 | WIPO ...................................... 602/16 |

*Primary Examiner*—Jerome Donnelly
*Attorney, Agent, or Firm*—Edwin D. Schindler

[57] ABSTRACT

An orthosis for supporting the foot, in particular when the foot is paralysed by lesions of the peroneal muscle or nerve, consists of a calf-supporting rail and of a foot support interconnected at the height of the ankle by a joint whose axis of rotation is substantially perpendicular to the side surface of the foot and which contains a spring whose resilient force acts to raise the front of the foot.

6 Claims, 1 Drawing Sheet

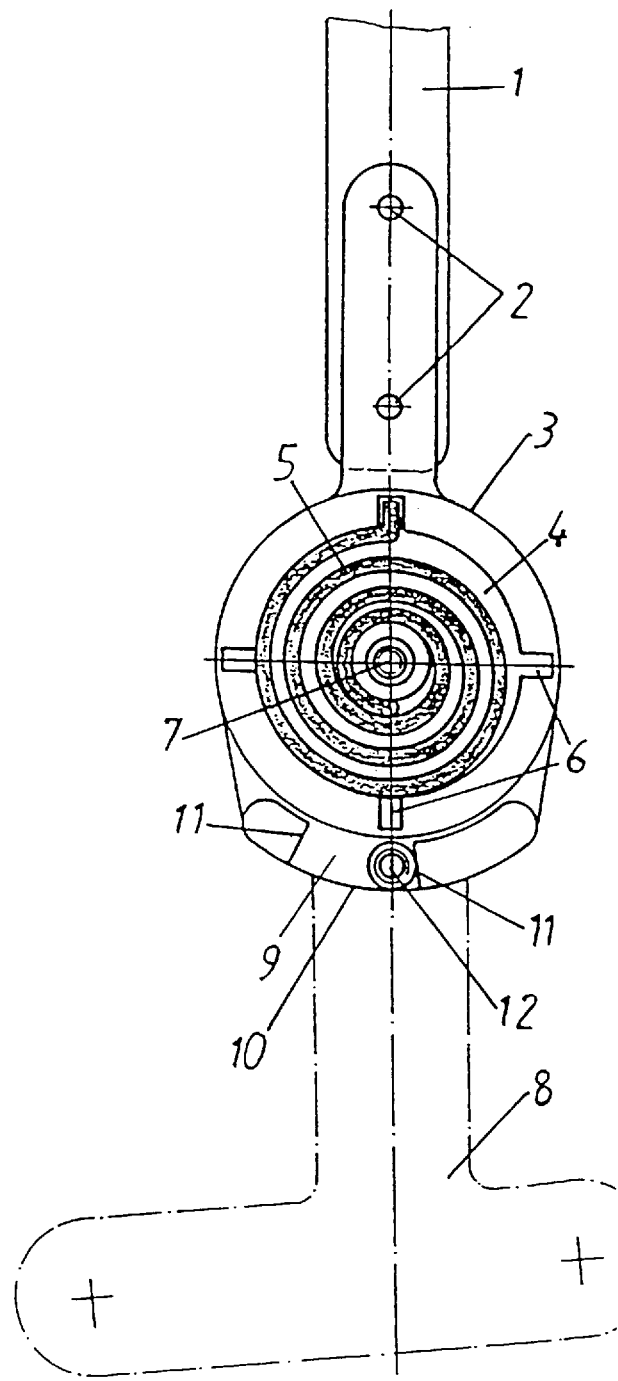

ORTHOSIS

BACKGROUND OF THE INVENTION

1. Technical Field of the Invention

The invention concerns an orthotic device to support the foot, especially in the case of paralyses, which are caused by damage to the peroneal muscle or the peroneal nerve, consisting of a splint and a foot support.

2. Description of the Prior Art

It is known, in the case of specific paralyses, to fix the foot by means of an orthotic device, the calf splint and foot support of which are connected to each other either rigidly and stationarily or through leaf springs. Such paralyses arise especially in the case of damage to the peroneal muscle or the peroneal nerve that controls it, as they may be caused for instance by the sequelae of apoplexy. The paralysis means that the concerned person is no longer able to control the foot consciously and as a result the foot drops downward and thereby turns inward, which is termed inversion or supination. Owing to this turning movement there is a risk of irreversible damage if walked upon.

Orthotic devices to support the foot are known in two embodiments. In one embodiment the calf splint is connected stationarily to the foot support, whereby the foot support and the calf splint form an angle of approx. 90°. Through this, the foot is rigidly fixed. The disadvantage thereby is that the orthotic device not only prevents a turning of the foot inwards, an upward and downward movement in the joint is also impossible, which makes walking very difficult. Moreover, there is the risk of a stiffening of the ankle, as it is fully, rigidly fixed. With the other embodiment the foot support is connected by means of a lateral leaf spring assembly to the splint. Consequently, an upward and downward movement of the foot is possible in principle, however the spring power and the range of the spring cannot be adapted to the individual needs of the patient as no possibility worth mentioning for adjustments and setting is given. In addition, a defined rotation axis is not created.

SUMMARY OF THE INVENTION

On this basis it is the objective of the invention to develop an orthotic device to support the foot, especially in the case of impairment of the peroneal muscle or the peroneal nerve, in such a way that the foot is fixed in such a manner that a lateral turning is prevented, however an upward and downward movement of the foot is possible and the spring power, which acts in the direction of the upward movement of the toes, can be adapted to the individual needs of the patient.

In accordance with the invention this problem is solved therein that the calf splint and the foot support are connected through a hinge at the level of the ankle, the rotation axis of which lies essentially perpendicular to the lateral surface of the foot and contains a spring, the spring power of which acts in the direction of the upward movement of the toes. The orthotic device is mounted as follows: The calf splint lies against the calf and is connected by means of the hinge to the foot support, which is also enclosed by the shoe.

Since the foot muscles of the paralysed foot cannot be contracted, it drops downward and executes an inward turn. The orthotic device prevents on the one hand a lateral turning of the ankle and in the manner that the joint can only be moved in the upward and downward movement of the foot. This is achieved through the position of the rotation axis, which lies perpendicular on the lateral surface of the foot so that it coincides with a rotation axis of the ankle. On the other hand, dropping down is compensated for by the spring power that counteracts this movement, which is set in such a way that in the resting position of the foot it holds a balance with the gravitational force of the foot. During walking, the spring is deflected from this resting position which means that when the foot is lifted this returns to the resting position.

As the hinge is located immediately laterally besides the ankle, the ankle can be moved, only the lateral turning movement is prevented. The patient's walking is made significantly easier because the ankle is not rigidly fixed. Moreover, through the movement of the ankle a stiffening of the joint is counteracted.

In an appropriate way the spring power increases superproportionally with the deflection of the spring. This has the advantage that the dynamics of the turning movement is more like the normal walking process and therefore enables trouble-free walking.

DESCRIPTION OF THE PREFERRED EMBODIMENTS OF THE INVENTION

In an appropriate embodiment of the invention the initial tension in the spring is changeable. Thus the spring power can be adapted to the individual needs of the patient. Therefore, for instance, orthotic devices for children or adults do not have to contain different springs and can basically be manufactured uniformly. Nevertheless, of course the possibility still exists to mount springs of differing strength in the hinge.

The spring is advantageously a coil spring, whereby the central point of the coils lies on the rotation axis. The spring is then affixed at the inner end at the rotation axis and at the outer end at the inner wall of the hinge. Because the movement of the hinge is a rotational movement about an axis, the design solution with a coil spring is the easiest.

In a suitable embodiment the initial tension of the coil spring can be changed in that the outer end of the coil spring is affixable to different places. By this means the spring can either be more tensioned or more relaxed. The advantage of this solution lies therein that the initial tension of the spring is very easy and uncomplicated to change.

For example, the outer end of the coil spring can be affixed in radial drill-holes, which are provided in the interior wall of the hinge, by means of which places are created to which the end of the spring can be securely anchored.

In a further embodiment the spring is a helical spring, the spring power of which acts essentially tangentially upon an essentially radial bar which belongs to the part of the hinge that belongs to the foot support. In this way a torque is generated that acts in the same direction as does the orthotic device with coil spring.

The initial tension of the helical spring can, in contrast to the coil spring, be altered steadily and in that a screw displaces the end point of the spring and thus changes the spring length.

The length of the helical spring and the associated screw can be shortened in that the screw extends axially in the spring. The screw head can for example serve as the stop face of the spring whereby the screwing of the screw into the hinge can be effected with a sufficiently long screwdriver.

BRIEF DESCRIPTION OF THE DRAWING FIGURE

An embodiment of the invention is shown in the drawing and is described in greater detail below. It shows a side view of the orthotic device.

DETAILED DESCRIPTION OF THE DRAWING FIGURE

The drawing shows the calf splint (1) which is connected to the hinge (3) through two rivets (2). Hinge (3) has a round cross section and has a cavity (4) that also has a round cross section. The coil spring (5) is embedded in cavity (4) and affixed by its outer end in the top of the four radial drill-holes (6), which are incorporated in the side wall of hinge (3). The four radial drill-holes are radial in relation to the central point of hinge (3), have a rectangular cross section and form respectively an angle of 90°. The rotation axis (7) of the hinge (3) is connected on the one hand to the inner end of coil spring (5) as well as to the foot support (8). Below hinge (3) is located a guide bar (9), which is delimited from above by the outer wall of the hinge, from below through a concentric circular arc in relation to hinge (3) and from the left and right through rotation stop faces (11). In guide bar (9) extends a cylinder (12) with circular cross section which is connected to foot support (8). Thereby the rotation movement of foot support (8) is limited to the circular arc (10) between the two rotation stop faces (11).

I claim:

1. An orthotic device for supporting a person's foot, such as in cases of paralyses, said orthotic device comprising:

calf splint means;

foot support means for supporting a foot of a person;

spring means for biassing the foot of a person for movement of toes of the foot in an upward direction; and, hinge means and a housing therefor, said hinge means being connected to said calf splint means and including a spring drill recess space internally around said housing of said hinge means in which said spring means is housed, with a first end of said spring means being attached at a rotation axis of said hinge means, as being adapted for being received in said recess space, and a second end of said spring means being affixable to a side wall of said housing of said hinge means via radial drill-holes, with the initial tension of said spring means being changeable in that, at least, one end of said spring means is affixable at different points, and said rotation axis of said hinge means being attached, at one end, to said foot support means.

2. The orthotic device for supporting a person's foot according to claim 1, wherein spring power of said spring means increases superproportionally with deflection of said spring means.

3. The orthotic device for supporting a person's foot according to claim 1, wherein said spring means is a coil spring and a central point of said coil spring lies on the rotation axis.

4. The orthotic device for supporting a person's foot according to claim 1, wherein said spring means is a helical spring having spring power which acts substantially tangentially in relation to the rotation axis upon a radial bar.

5. The orthotic device according to claim 4, wherein the initial tension of said spring means is further changeable through a screw by means of which the length of said spring means is capable of being shortened or extended in the direction of the spring power.

6. The orthotic device according to claim 5, wherein said screw axially in said spring means.

* * * * *